United States Patent [19]

Pazik

[11] Patent Number: 4,960,916

[45] Date of Patent: Oct. 2, 1990

[54] ORGANOMETALLIC ANTIMONY COMPOUNDS USEFUL IN CHEMICAL VAPOR DEPOSITION PROCESSES

[75] Inventor: John C. Pazik, Alexandria, Va.

[73] Assignee: United States of America as represented by the Secretary of the Navy, Washington, D.C.

[21] Appl. No.: 415,505

[22] Filed: Sep. 29, 1989

[51] Int. Cl.$^5$ .............................. C07F 9/90; C07F 9/92
[52] U.S. Cl. ....................................... 556/70
[58] Field of Search ........................................ 556/70

[56] References Cited

U.S. PATENT DOCUMENTS

| | | | |
|---|---|---|---|
| 3,975,218 | 8/1976 | Ruehrwein | 148/175 |
| 4,010,045 | 4/1976 | Ruehrwein | 148/174 |
| 4,377,528 | 3/1983 | Beach et al. | 556/70 X |
| 4,404,408 | 9/1983 | Wirth et al. | 556/70 X |
| 4,734,514 | 3/1988 | Melas et al. | 556/70 |

*Primary Examiner*—Arthur C. Prescott
*Attorney, Agent, or Firm*—Thomas E. McDonnell

[57] ABSTRACT

Organometallic antimony compounds having increased stability that are useful in chemical vapor deposition processes are provided which comprise stibines containing sterically-demanding ligands, stibines lacking beta hydrogen atoms, or aromatic stibines. These compounds will generally have the formula:

$$SbR_nX_{3-n}$$

wherein R is selected from the group consisting of neopentyl, 2-ethylbutyl, 1-ethylpropyl, perhaloalkanes having 3–5 carbon atoms, benzyl, fluoro-substituted phenyl, cyclopentyl, and pentamethylcyclopentadienyl; X is selected from the group consisting of Br, Cl, I and H; and wherein n is an integer from 1 to 3. These compounds exhibit increased thermal stability and are thus advantageously used as substitutes for arsenic or other group V metals in chemical vapor deposition processes. Because of the bulky ligand group bound to the antimony and/or the lack of beta hydrogen atoms in the ligand, theses organometallic stibines are less prone to decompose prematurely and thus exhibit greater thermal stability than previously known alkyl antimony hydride compounds.

8 Claims, No Drawings

ORGANOMETALLIC ANTIMONY COMPOUNDS USEFUL IN CHEMICAL VAPOR DEPOSITION PROCESSES

FIELD OF THE INVENTION

The invention relates to organometallic antimony compounds and their halide derivatives which are useful as sources or precursors for sources in chemical vapor deposition (CVD) processes such as those employed in the fabrication of semiconductors.

BACKGROUND OF THE INVENTION

Chemical vapor deposition (CVD) processes, and more particularly, organometallic chemical vapor deposition (OMCVD or MOCVD) processes are commonly employed in the semiconductor, optical, and optoelectronic industries for doping or coating a suituable substrate. These processes essentially involve the depositing of a dopant or a thin metal film on a substrate such as silicon. The deposited films can be sources of doping impurities which are driven into the substrate, or the films themselves can have different electrical or optical properties than the substrate. The properties of the film are based primarily on the conditions involved in the deposition and the chemical identity of the deposited film itself. OMCVD processes are particularly advantageous in that organometallic compounds can be found which have significantly higher vapor pressures at moderate temperatures than the corresponding metals. As a result, these compounds decompose to release the corresponding metals or form compounds thereof at those deposition temperatures normally used in the fabrication of semiconductors and other materials.

Typically, in the semiconductor art, fabrication of III-V semiconductors, e.g., gallium arsenide, occurs through a reaction of a group III organometallic source of the type M(III)R$_3$, wherein M(III)=Al, In or Ga and R is a lower alkyl, with a group V hydride of general formula M(V)H$_3$, wherein M(V)=P or As. This process has major disadvantages in that in that the group V hydrides used in the reaction are extremely toxic, and their gaseous nature makes them exceedingly dangerous to transport and handle. Furthermore, large excesses of these toxic hydrides are generally required to successfully produce high quality films. Because of these problems, alternative materials have been sought which can be used successfully to produce high quality Group III/Group V films in a safe and effective manner.

Toxicity associated with group V hydride sources has led to the recent development of hydrocarbon-substituted analogs of the type M(V)R$_n$H$_{3-n}$ (wherein n=1 or 2) which can be used more safely in vapor deposition applications such as described above. These compounds, such as described in U.S. Pat. No. 4,734,514, are primarily directed only to the group V metals arsenic (As) and phosphorus (P), and not to antimony (Sb) compounds. The primary reason for the exclusion of antimony from these analogs is the fact that among the group V congeners, i.e., N, P, As and Sb, a sharp division exists in the chemistry of organometallic compounds between N-, P- and As-containing compounds on the one hand, and Sb-containing compounds on the other. For example, the hydrides NH$_3$, PH$_3$ and AsH$_3$ are quite stable at room temperature, yet SbH$_3$ (stibine) rapidly decomposes to Sb metal and H$_2$ at similiar temperatures. Further, the methyl and ethyl group V hydride compounds such as NR$_n$H$_{3-n}$, PR$_n$H$_{3-n}$ and AsR$_n$H$_{3-n}$ (wherein R=ethyl or methyl and n=1 or 2) are all stable at room temperature, whereas antimony compounds SbEt$_n$H$_{3-n}$ and SbMe$_n$H$_{3-n}$ (Et=ethyl, Me=methyl and n=1 or 2) all decompose at relatively low temperatures. Consequently, one cannot assume the existence of certain Sb compounds, particularly those of the hydrides, on the basis of the existence of the corresponding N, P, and As compounds. It is clear that if one wishes to employ Sb-containing organometallic compounds in the chemical vapor deposition processes described above, one must first overcome their problems with regard to thermal stability. Although Sb(CH$_3$)$_3$ is thermally stable and is currently used as an Sb source for narrow bandgap semiconductors comprised of InSb, a thermally stable Sb source having at least one hydrogen atom bound to Sb would be preferable.

An examination of the features of the lower alkyl groups methyl, ethyl, propyl and butyl reveals that they all have a relatively small size and/or the presence of beta-hydrogens. The presence of beta-hydrogen atoms is believed to be responsible for the decomposition of organometallic compounds such as Ga(CH$_2$CH$_2$CH$_2$CH$_3$)$_3$, and may also provide a decomposition route in the chemistry of compounds such as As[C(CH$_3$)$_3$]H$_2$. It further appears that ligands of small size may facilitate disproportionation reactions. These features, either individually or in combination, may well account for the instability of antimony compounds incorporating these groups. It is thus highly desirable to use this knowledge to overcome the problems of thermal instability associated with antimony hydrides and develop organometallic antimony compounds which are easy to synthesize, thermally stable, and which can be used safety and effectively as a source or an intermediate in chemical vapor deposition.

SUMMARY OF THE INVENTION

It is therefore an object of the present invention to develop novel antimony compounds which are useful as sources or precursors for sources in organometallic vapor deposition processes, particularly the CVD fabrication of semiconductors such as narrow bandgap semiconductors.

It is further an object of the present invention to provide new antimony hydride sources which overcome the problems of thermal instability that limit their usefulness as CVD sources.

It is still further an object of the present invention to provide a stable antimony hydride source useful in OMCVD processes which utilizes sterically demanding ligands and/or ligands which lack a beta hydrogen atom.

These and other objects are provided in the present invention which comprises novel, thermally stable antimony compounds having a general formula:

SbR$_n$X$_{3-n}$ wherein R is selected from the group consisting of neopentyl, 2-ethylbutyl, 1-ethylpropyl, perhaloalkanes having 3-5 carbon atoms, benzyl, fluoro-substituted phenyl, cyclopentyl, and pentamethycyclopentadienyl; X is selected from the group consisting of Br, Cl, I and H; and n is an integer from 1 to 3.

In particular, antimony hydride compounds in accordance with the present invention which are suitable for use in chemical vapor deposition processes will be those which lack beta-hydrogen atoms and/or include sterically-demanding ligands, both features which make the compound less likely to decompose under normal conditions. It is also contemplated in the present invention that the new aromatic stibines will exhibit increased thermal stability over those currently known and thus will also be suitable for use as an antimony source in OMCVD processes.

DETAILED DESCRIPTION OF THE PREFERRED EMBODIMENTS

According to the present invention, organometallic antimony compounds useful in chemical vapor deposition processes are provided which comprise stibines possessing organic substituents having sterically hindered groups and/or lacking a beta hydrogen atom. In general, when physically small groups such as lower alkyl ligands and groups containing beta hydrogen atoms are present, certain types of decomposition mechanisms can be promoted. The presence of small groups can accelerate decomposition which proceeds through a disproportionation process, while the presence of beta hydrogen atoms can lead to decomposition via a beta hydrogen elimination mechanism.

The compounds of the present invention overcome one or both of these problems. The absence of a beta hydrogen atom in the organic substitutents prevents decomposition by the elimination mechanism. Additionally, the bulky organic groups used to promote steric hindrance make the compounds less likely to undergo disproportionation. The decreased reactivity, characteristic of compounds in accordance with the present invention, prevents premature decomposition and thus results in increased stability. The nature of the compounds useful in the present invention is very dependent upon the characteristics imparted by their attached ligands, and thus the compounds of the invention that are most suitable for use in chemical vapor desposition processes are those which lack a beta hydrogen atom and which contain a bulky organic group.

In general, a compound in accordance with the present invention will have the structure:

$SbR_nX_{3-n}$ wherein R is selected from the group consisting of neopentyl, 2-ethylbutyl, 1-ethylpropyl, perhaloalkanes having 3–5 carbon atoms, benzyl, flouro-substituted phenyl, cyclopentyl, and pentamethylcyclopentadienyl; X is selected from the group consisting of Br, Cl, I and H; and n is an integer from 1 to 3.

These compositions will include stibines possessing organic substitutents having either sterically hindered groups, lack of beta hydrogen atoms, or both. The fluorophenyl substitutents suitable in this compound include di-, tri-, tetra-, penta- and hexafluorinated compounds.

It is particularly preferred to employ the neopentyl stibine of the present invention in chemical vapor deposition processes. Neopentyl is a particularly preferred substitutent because it has both steric hindrance and no hydrogen present at the beta-carbon. Neopentyl-substituted stibines are less reactive at room temperature at least in part as a result of the bulky neopentyl group. The lack of beta hydrogen atoms in the neopentyl stibine of the invention contributes to the greater thermal stability of these compounds since many decomposition mechanisms involve beta hydrogen elimination. Also, these properties which increase thermal stability may be important during the chemical deposition processes which occur at very high temperatures. Increased thermal stability may prevent premature decomposition, and this is particularly important in the antimony compounds since most primary and secondary stibines decompose at or near room temperature, thereby rendering them useless as sources for CVD processes. The neopentyl group, for example, offers the unique opportunity to prepare a stable primary or secondary stibine for CVD use. No primary or secondary stibines are currently available for CVD use.

In general, therefore, one class of compounds in accordance with the present invention are those stibines with ligands which lack a beta hydrogen atom. In addition to neopentyl stibine ($Sb(CH_2CMe_3)H_2$, wherein Me=methyl) described above, exemplary of such stibine compounds are bisneopentyl stibine ($Sb(CH_2CMe_3)_2H$), perfluoropropyl stibine ($Sb(CF_2CF_2CF_3)H_2$), bisperfluoropropyl stibine ($Sb(CF_2CF_2CF_3)_2H$), and isomers of these compounds. In addition, halogens such as Br, Cl or I can be substituted for the hydrogen bonded directly to the antimony.

A second class of stable stibine compounds provided in accordance with the present invention are those which contain sterically-demanding ligands. Among these include compounds such as 2-ethylbutyl stibine ($SbCH_2CH(CH_2CH_3)_2H_2$), bis-2-ethylbutyl stibine ($Sb[CH_2CH(CH_2CH_3)]_2H$), 1-ethylpropylstibine ($SbCH(CH_2CH_3)_2H_2$), bis-1-ethylpropylstibine ($Sb[CH(CH_2CH_3)_2]_2H$), cyclopentylstibine ($Sb(C_5H_{10})H_2$), biscyclopentyl stibine ($Sb(C_{10}H_{20})H$), and isomers of the above. Among these compounds, the cyclopentyl stibines also have sterically demanding ligands, and thus offer similar advantages to those compounds having neopentyl ligands, particularly in terms of increased stability relative to disproportionation.

It is also the case that aromatic groups can be used in the antimony compounds of the present invention to give a more stable stibine suitable for use in chemical vapor deposition processes. Accordingly, compounds provided in accordance with the present invention also comprise those having the following formulas:

| |
|---|
| $Sb(C_6F_5)X_2$ |
| $Sb(C_6F_5)_2X$ |
| $Sb(C_6F_3)X_2$ |
| $Sb(C_6F_3)_2X$ |
| $Sb(C_5(CH_3)_5)X_2$ |
| $Sb(C_5(CH_3)_5)_2X$ | wherein X is selected from the group consisting of Br, Cl, I and H.

Aromatic groups can be employed to create aromatic stibines in accordance with the present invention most likely due to their increased stability when compared to the typical alkyl antimony derivatives. The aromatic stibines as described in this invention also lack beta hydrogens, and this increases their stability. The pentamethylcyclopentadienyl ligand is of particular interest because in addition to lacking beta hydrogen atoms, it is also a sterically demanding group.

In addition to the direct use of the compounds mentioned above in chemical vapor deposition processes, their use as starting materials for the synthesis of primary and secondary stibine sources is also contemplated by the invention. The new compounds provided by the present invention, especially the halogenated compounds, have a tremendous value as starting materials for the formation of CVD sources, such as would be required in the fabrication of semiconductors. As an example, trineopentyl stibine (SbNp$_3$, wherein Np=neopentyl) is useful as a starting material for the synthesis of primary and secondary neopentyl stibine as is indicated below:

SbNp$_3$ + Br$_2$ ⟶ SbNp$_3$Br$_2$

SbNp$_3$Br$_2$ ⟶ SbNp$_2$Br + NpBr

4SbNp$_2$Br + LiAlH$_4$ ⟶ 4SbNp$_2$H + LiBr + AlBr$_3$

SbNp$_2$Br + Br$_2$ ⟶ SbNpBr$_2$ + NpBr

2SbNpBr$_2$ + LiAlH$_4$ ⟶ 2SbNpH$_2$ + LiBr + AlBr$_3$

The compounds of the present invention are thus advantageously used as both sources and precursors to sources used in the various chemical vapor deposition processes. In particular, these compounds are especially useful in the chemical vapor deposition fabrication of semiconductors such as narrow bandgap semiconductors comprised of InSb.

It is contemplated that a number of conventional methods known in the art will be used to prepare the novel stibine compound of the present invention. However, in general, the triorgano-stibines of the present invention are preferably prepared by reacting the corresponding halides with a metallic alkylating agent. Preparation of these compounds, as exemplified by the preparation of neopentyl stibine, may be accomplished as follows:

a. SbX$_3$ + nLiCH$_2$C(CH$_3$)$_3$ ⟶ Sb(CH$_2$C(CH$_3$)$_3$)$_n$X$_{3-n}$ + nLiX (n = 1,2, or 3   X = Cl, Br or I)

b. SbX$_3$ + nMgCH$_2$C(CH$_3$)$_3$X ⟶

Sb(CH$_2$C(CH$_3$)$_3$)$_n$X$_{3-n}$ + nMgX$_2$ (n = 1 or 2   X = Cl, Br or I)

In addition, zinc and mercury alkylating compounds also result in the formation of neopentyl stibines, and it is conceivable that alternative synthesis routes may also be employed.

With regard to organo-antimony (III) halides, these are preferably prepared by reductive elimination from the appropriate metal (V) halide or by stoichiometric reaction with metallic alkylating agents. For example, the neopentyl stibine halide deriviates, SbNp$_2$Br and SbNpBr$_2$ (Np=neopentyl) have been synthesized by reductive elimination of NpBr from SbNp$_3$Br$_2$ and SbNp$_2$Br$_3$, respectively. Primary and secondary stibines are synthesized from the reaction of an antimony halide with lithium aluminum hydride in tetraglyme or diethylether.

The novel stibine compounds of the present invention can thus be useful in a number of chemical vapor deposition processes, particularly those involving fabrication of semiconductors. The unique characteristics of these compounds, particularly the absence of beta hydrogen atoms in the ligands and/or the steric hindrance of a bulky organic group, make these compounds stable and thus particularly suitable for use in organometallic chemcial vapor deposition processes.

The following examples are provided to further exemplify the production of compounds of the present invention. These examples are presented for illustrative purposes only, and are not in any way intended to limit the scope of the present invention. It is further contemplated that alternative synthesis methods may be used by those of ordinary skill of the art to manufacture the compounds of the present invention:

EXAMPLE 1

Synthesis of SbNp$_3$

A 100 ml reaction bulb equipped with a Teflon stopcock is charged with 1.221 g of Mg powder (50.252 mmol). Neopentyl chloride (4.6542 g, 43.66 mmol) and diethyl ether (ca. 30 mL) are then vacuum distilled into the reaction bulb. The reaction mixtures are subjected to ultrasound for 1 hr., and then the mixture is stirred and refluxed in the sealed bulb for 15 hr. The bulb is then connected to a 100 mL two neck flask by means of a 12/30 joint. The flask is next evacuated and charged with 2.658 g of SbCl$_3$ (1.652 mmol) and 40 ml of diethyl ether. The solution of NpMgCl is added over the course of 20 min. to the SbCl$_3$ solution at 0° C. A voluminous precipitate of MgCl$_2$ is observed. The reaction mixture is warmed to room temperature and stirred for 24 hr. After the ether is removed by vacuum distillation, the reaction flask is connected to a side arm flask by means of an 80° elbow. Trineopentylstibine is isolated by vacuum distillation, at 100°, into the cooled (−196° C.) side arm flask. Residual quantities of ether are then removed by vacuum distillation. Small quantities of MgCl$_2$ are removed to form the product by filtration through a fine glass frit, yielding SbNp$_3$ as the colorless, pentane-soluble crude product. The SbNp$_3$ is finally purified by vacuum sublimation at 50°-60° C. (0.001 mm).

EXAMPLE 2

Synthesis of SbNp$_3$Br$_2$

A 100 mL flask is charged with SbNp$_3$ (1.310 g, 3.908 mmol) and approximately 50 mL of pentane is vacuum distilled on the SbNp$_3$. A previously weighed sample of bromine (0.6324 g, 3.957 mmol) is then vacuum distilled into the reaction flask. The reaction mixture is allowed to slowly warm to room temperature with stirring. The red mixture immediately forms a white precipitate of SbNp$_3$Br$_2$ at room temperature. The reaction mixture is stirred for ½ hr. The reaction solvent is then removed by vacuum distillation, and the reaction flask is fitted with a medium frit and a side arm receiving flask. Pentane (15 mL) is vacuum distilled into the flask containing the reaction product, and the SbNp$_3$Br$_2$ is purified by being washed twice with the pentane.

EXAMPLE 3

Synthesis of an SbNp$_2$Br/SbNpBr$_2$ mixture

A 100 mL bulb with a Teflon valve is charged with a sample of SbNp$_3$Br$_2$ (1.657 g, 3.348 mmol). The bulb is evacuated and heated to 290° C. for approximately ½ hour producing a yellowish brown liquid (a grayish precipitate was also observed at this point). The most volatile product, mostly NpBr, is then removed by vacuum distillation. Neopentyl bromide has only beeni-dentified by its $^1$H NMR spectrum in benzene solution. The less volatile components, crude SbNp$_2$Br and SbNpBr$_2$, were separated from the remaining solid product by distillation in a short path, still under dynamic vacuum. The SbNp$_2$Br/SbNpBr$_2$ mixture was obtained as a yellow liquid and characterized by $^1$H NMR spectroscopy.

EXAMPLE 4

Synthesis of SbNp$_2$H and SbNpH$_2$

A mixture of the antimony halides, SbNpBr$_2$ and SbNp$_2$Br (0.8669 g) was placed in a tared addition tube to which was added ca. 5 mL of tetraglyme. The tube was then connected to the side arm of a 100 mL 2-neck flask containing 0.0339 g (0.893 mmol) of lithium aluminum hydride (LAH) suspended in 25 mL of tetraglyme. The LAH mixture was stirred at room temperature for 18 hr. and then cooled to −15° C. Addition of the halide solution over a period of 5–10 min. resulted in the formation of a brown mixture. The reaction mixture was stirred for 2 hr. at −15° C. and for 1 hr. at ambient temperature. The product mixture SbNpH and SbNp$_2$H was then separated from the reaction mixture by vacuum distillation.

What is claimed is:

1. A compound having the formula:

$$SbR_nX_{3-n}$$

wherein R is selected from the group consisting of neopentyl, 2-ethylbutyl, 1-ethylpropyl, perhaloalkanes having 3–5 carbon atoms, benzyl, fluoro-substituted phenyl, cyclopentyl, and pentamethylcyclopentadienyl;

X is selected from the group consisting of Br, Cl, I and H; and n is an integer from 1 to 3.

2. An organometallic antimony compound useful in chemical vapor deposition processes comprising a compound selected from the group consisting of stibines containing a sterically-demanding ligand, stibines with a ligand lacking a beta hydrogen atom, and aromatic stibines.

3. An organometallic antimony compound according to claim 2 comprising a stibine containing a sterically-demanding ligand.

4. An organometallic antimony compound according to claim 3 comprising a compound selected from the group consisting of neopentylstibine, 2-ethylbutyl stibine, bis-2-ethylbutyl stibine, 1-ethylpropylstibine, bis-1-ethylpropylstibine, cyclopentyl stibine, biscyclopentyl stibine, and isomers of the above.

5. An organometallic antimony compound according to claim 2 comprising a stibine with a ligand lacking a beta hydrogen.

6. An organometallic antimony compound according to claim 5 comprising a compound selected from the group consisting of neopentyl stibine, bisneopentyl stibine, perfluoropropyl stibine, bisperfluoropropyl stibine, and isomers of the above.

7. An organometallic antimony compound according to claim 2 comprising an aromatic stibine.

8. An organometallic antimony compound according to claim 7 comprising a compound selected from the group consisting of
Sb(C$_6$F$_5$)X$_2$, Sb(C$_6$F$_5$)$_2$X, Sb(C$_6$F$_3$)X$_2$,
Sb(C$_6$F$_3$)$_2$X, Sb(C$_5$(CH$_3$)$_5$)X$_2$, and
Sb(C$_5$(CH$_3$)$_5$)$_2$X, wherein X is selected from the group consisting of Br, Cl, I and H.

* * * * *